United States Patent [19]

Koga et al.

[11] 4,289,965
[45] Sep. 15, 1981

[54] EMISSION COMPUTED TOMOGRAPH

[75] Inventors: Kenichiro Koga; Yoshiharu Hirose, both of Kyoto; Iwao Kanno, Akita; Kazuo Uemura, Akita; Shuichi Miura, Akita, all of Japan

[73] Assignee: Shimadzu Corporation, Japan

[21] Appl. No.: 112,637

[22] Filed: Jan. 16, 1980

[30] Foreign Application Priority Data

Jan. 23, 1979 [JP] Japan .................. 54-8120[U]

[51] Int. Cl.³ .................. G01T 1/20; G21F 5/04
[52] U.S. Cl. .................. 250/363 S; 250/513
[58] Field of Search .......... 250/363 S, 445 T, 505, 250/511, 513

[56] References Cited

U.S. PATENT DOCUMENTS

| | | | |
|---|---|---|---|
| 3,982,133 | 9/1976 | Jupa et al. | 250/505 |
| 4,118,632 | 10/1978 | Luig | 250/505 |
| 4,150,292 | 4/1979 | Ter-Pogossian | 250/445 T |

Primary Examiner—Alfred E. Smith
Assistant Examiner—Janice A. Howell
Attorney, Agent, or Firm—Fidelman, Wolffe & Waldron

[57] ABSTRACT

An emission computed tomograph provided with different types of collimators for selective use with different kinds of radionuclides. The different collimators are alternatively brought into operative position in front of the radiation detector in accordance with the kind of radionuclide being used.

6 Claims, 6 Drawing Figures

EMISSION COMPUTED TOMOGRAPH

BACKGROUND OF THE INVENTION

This invention relates to an emission computed tomograph.

Emission computed tomography commonly referred to as ECT is a technique for obtaining an image of the distribution of radioactivity of radioisotope within a desired plane perpendicular to the axis of the body of a patient being examined by administering to the patient a pharmaceutical compound labelled with the radioisotope, detecting from outside the body the radiation such as X-rays or gamma ($\gamma$) radiation emitted by the isotope that has been accumulated in a region or organ of the body of the patient, and processing the detected data by an electronic computer.

Gamma radiation emitting radionuclides such as $^{133}$Xe, $^{99m}$Tc and $^{81m}$Kr or positron emitting radionuclides such as $^{11}$C, $^{13}$N and $^{15}$O are used as the radioisotope. Since the two types of radionuclides have different emission characteristics, it has been customary to design an apparatus for exclusive use with a particular kind of radionuclides, so that different types of apparatus must be used with different kinds of radionuclides. This certainly is inconvenient and uneconomical.

Accordingly, the primary object of the invention is to provide an emission computed tomograph which can be used with different kinds of radionuclides with a short conversion time.

Another object of the invention is to provide such an emission computed tomograph as aforesaid which is simple in construction with a relatively small number of movable component parts and therefore is reliable in operation.

Another object of the invention is to provide such a emission computed tomograph as aforesaid which requires a relatively short time for measurement.

The invention will be described in detail with reference to the accompanying drawing.

SUMMARY OF THE INVENTION

In accordance with the invention, there are provided two types of collimators, one for use with gamma radiation emitting radionuclides and the other for use with positron emitting radionuclides, and the two types of collimators are selectively positioned in front of the radiation detectors in accordance with the kind of radionuclide being used.

DESCRIPTION OF PREFERRED EMBODIMENTS

Figure 3:
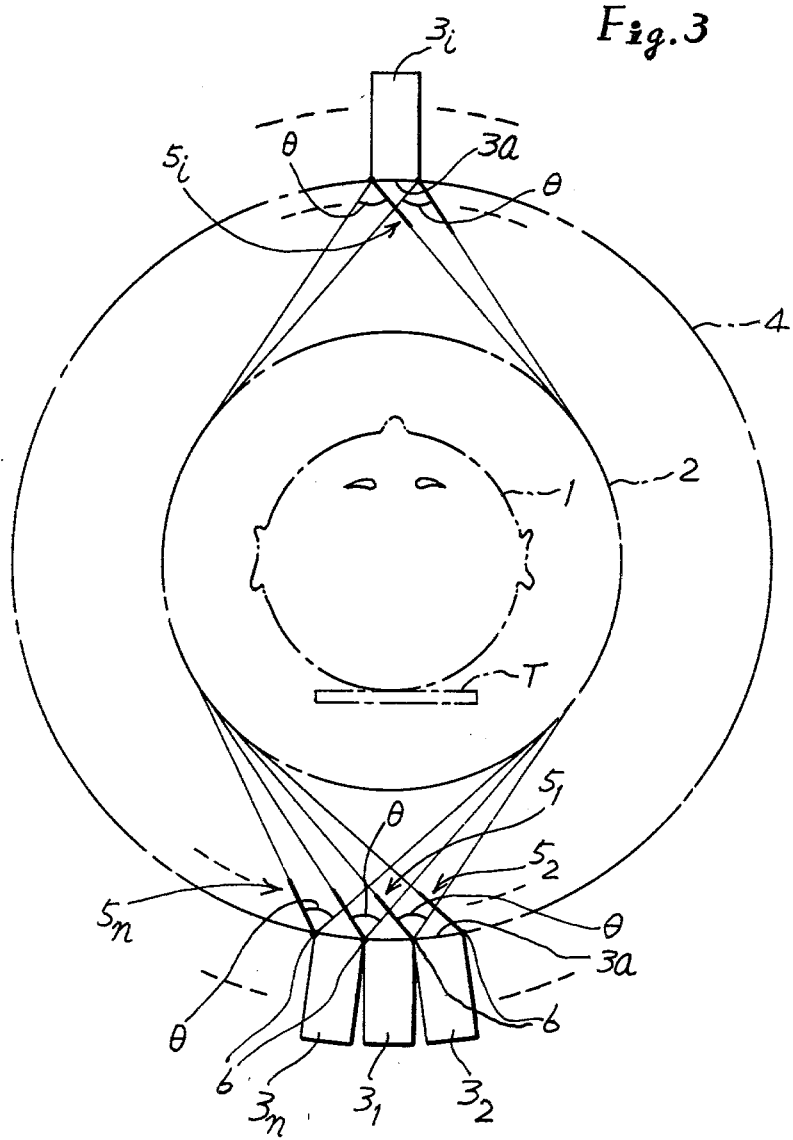
FIG. 3 schematically shows the arrangement of the swing collimators for use with gamma radiation emitting radionuclides.
Figure 4:
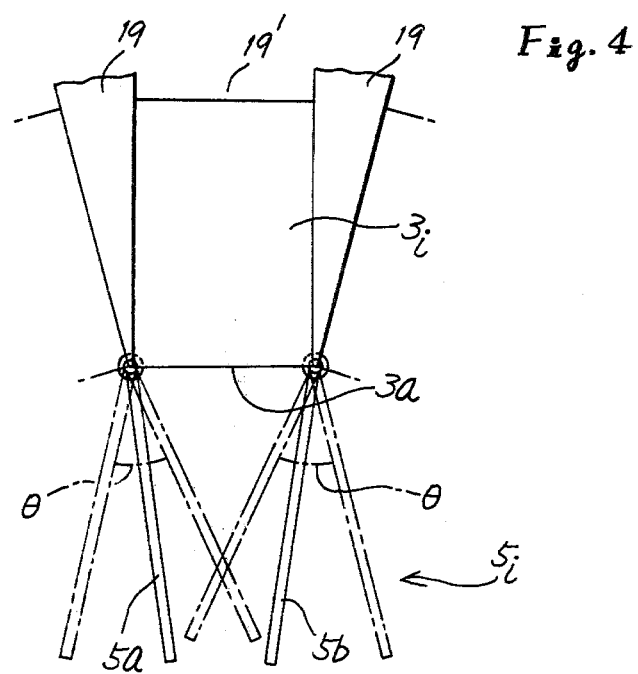
FIG. 4 is a somewhat schematic enlarged top plan view of one of the swing collimators of FIG. 3.
Figure 5:
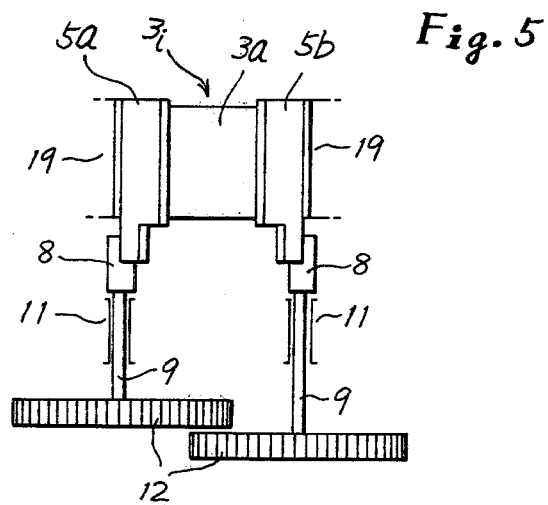
FIG. 5 is an elevational view of the swing collimator as viewed from below in FIG. 4.

FIGS. 4 and 5 somewhat schematically show an example of the former type of collimator, and FIG. 3 schematically shows the arrangement of a plurality of such collimators relative to the radiation detectors.

Referring to FIG. 3, a part of a human body, e.g., the head 1 to be examined is shown in an area 2, within which it is possible to reconstruct tomographic images of the object being examined.

A plurality of radiation detectors $3_1, 3_2, \ldots 3_i, \ldots 3_n$ are circumferentially arranged side by side and radially directed with their planes $3a$ on which the radiation is incident being arranged along a circle 4 concentric with the circle defining the area 2. These detectors form a circular ring so that they will be referred to collectively as the detector ring 3.

A plurality of swing collimators $5_1, 5_2, \ldots 5_i, \ldots 5_n$ for use with gamma radiation emitting radionuclides are circumferentially arranged radially inwardly of the circle 4 so that they can selectively be brought in front of or removed from before the detectors $3_1, 3_2, \ldots 3_i, \ldots 3_n$, as will be described later in detail. Since the swing collimators as a whole form a circular ring, they will be referred to collectively as the swing collimator ring 5. Each of the swing collimators comprises a pair of thin plates $5a$ and $5b$ made of a material such as lead or tungsten which is capable of blocking penetration of X-rays or gamma radiation therethrough. Each of the plates $5a$ and $5b$ is pivotally supported at a point 6 on the circle 4 between each adjacent two of the detectors so that the plates $5a$ and $5b$ are swingable through an angle $\theta$ subtended by the two straight lines extending from each of the points 6 and being tangential to the circle defining the area 2. The angle $\theta$ is sufficient to cover the whole of the object to be examined. The plates $5a$ and $5b$ of all the collimators $5_1, 5_2, \ldots 5_i, \ldots 5_n$ are swung simultaneously and at the same angular speed by a suitable drive to be described below.

Figure 1:
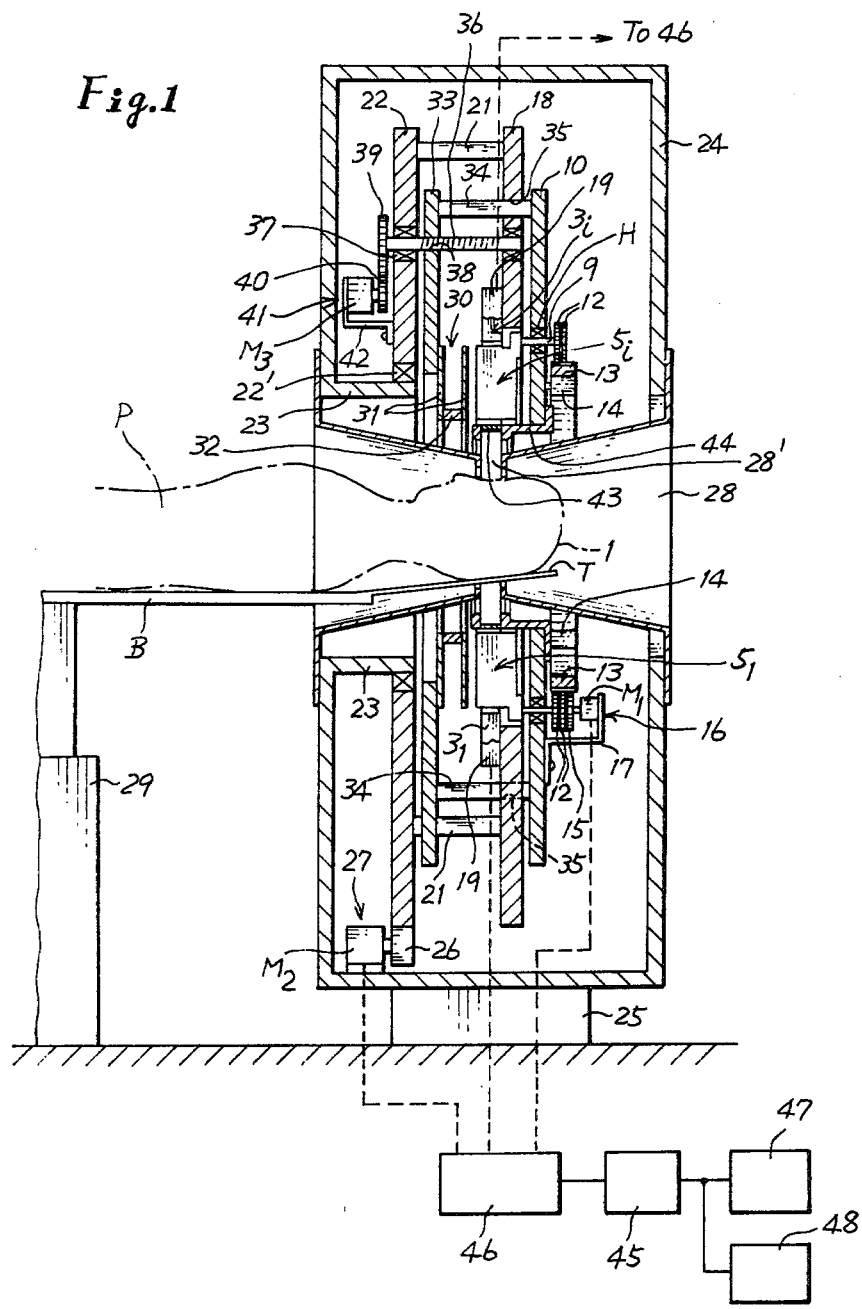
FIG. 1 is a somewhat schematic elevational view, in vertical section, of one embodiment of the invention.
Figure 2:
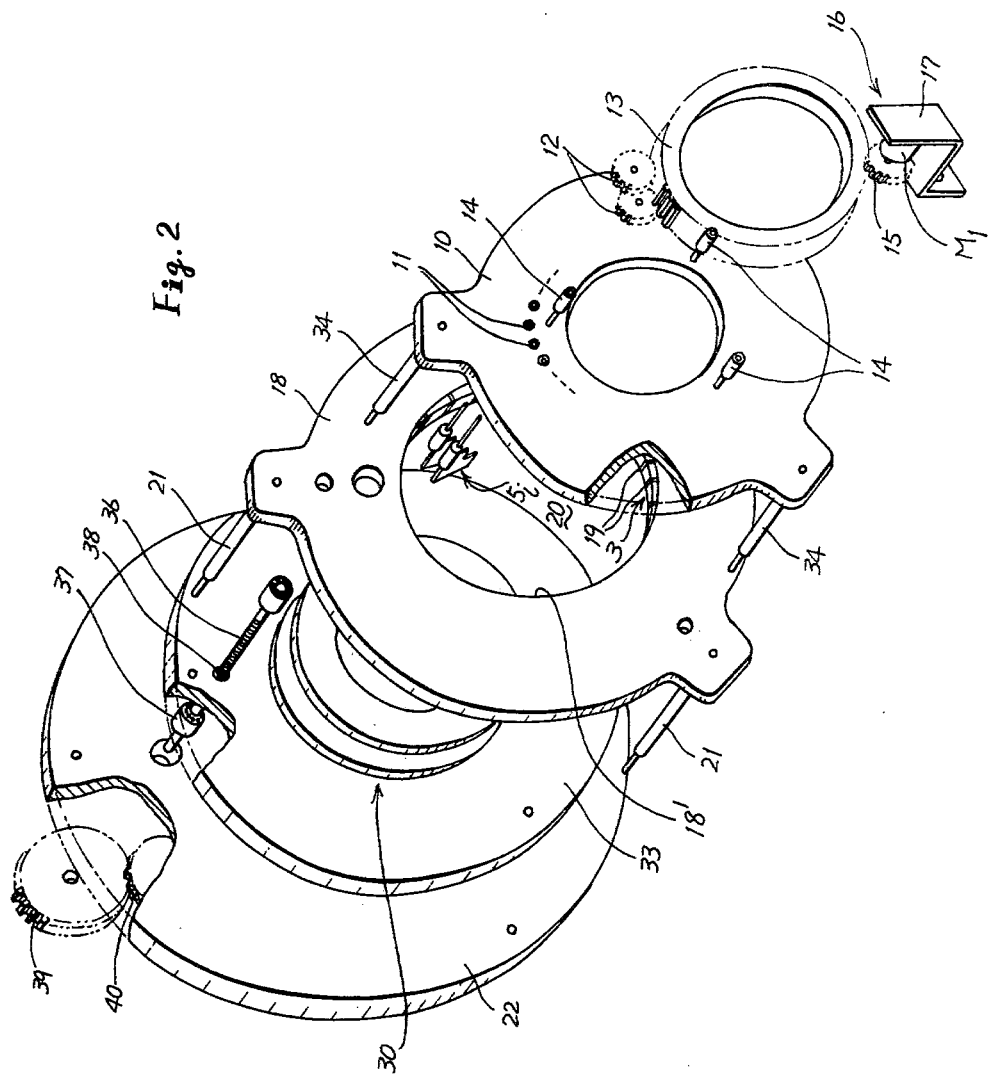
FIG. 2 is an exploded view of the apparatus shown in FIG. 1, with some of the component parts being omitted for simplicity of illustration.

As shown in FIGS. 4 and 5, each of the plates $5a$ and $5b$ of the swing collimator is formed with a boss 8 to which one end of a shaft 9 is fixed. As shown in FIGS. 1 and 2, an annular plate 10 supports the shafts 9 of the plates $5a$ and $5b$ of all the swing collimators by means of a series of bearings 11 (only a few of which are shown in FIG. 2) arranged circumferentially in the annular support plate 10, so that the plates $5a$ and $5b$ are circumferentially arranged and radially directed at one axial side of the annular plate 10.

The shaft 9 of each of the plates $5a$ and $5b$ passes through the annular plate 10 so as to project from the opposite axial side thereof with a gear 12 fixed to the opposite end of the shaft 9. The gears 12 thus fixed to the shafts 9 of the plates of all the collimators $5_1, 5_2, \ldots 5_i, \ldots 5_n$ are circumferentially arranged on one axial side of the plate 10, although only two of the gears 12 are shown in FIG. 2 for simplicity of illustration. The gears 12 mesh with a large ring gear 13 which is rotatably mounted on the plate 10 by means of three rollers 14. The gears 12 are alternately displaced axially by a distance corresponding substantially to the thickness of the gear 12 as shown in FIG. 5 so that all the gears 12 are arranged circumferentially about the ring gear 13 and mesh therewith.

A drive pinion 15 also meshes with the ring gear 13 and is rotated by a suitable driving device 16 including a reversible motor $M_1$ and fixed to the support plate 10 by a bracket 17. The drive pinion 15 is also displaced axially from the gears 12 to enable meshing of the pinion 15 with the ring gear 13. As can be understood from the above description, the ring gear 13 has an axial thickness corresponding to at least the sum of double the axial thickness of the gear 12 and the axial thickness of the pinion 15.

It will be easily seen that upon rotation of the motor $M_1$ of the driving device 16 in either direction the plates 5a and 5b of all the collimators $5_1, 5_2, \ldots 5_i, \ldots 5_n$ are simultaneously swung in the same direction of the same angular speed.

Figure 6:
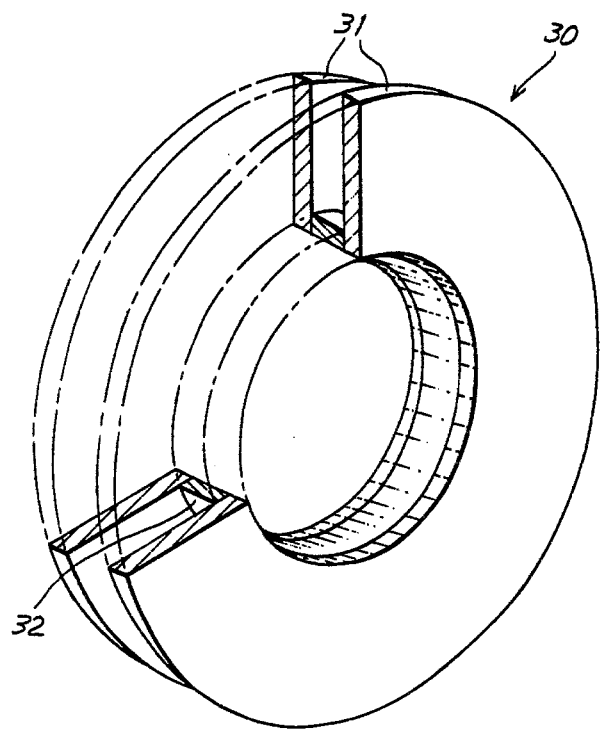
FIG. 6 is a perspective view, partly cut away, of the bobbin collimator for use with positron emitting radionuclides.

FIG. 6 shows an example of the collimator for use with positron emitting radionuclides. The collimator 30 comprises a pair of annular plates or flanges 31 connected by a spacer ring 32 in axially aligned and spaced apart parallel relation to each other. The flanges 31 are made of a material such as lead or tungsten capable of blocking penetration of positron annihilation radiation. The outer diameter of the flanges 31 is slightly smaller than the diameter of the circle 4. The collimator 30 may be referred to as the "bobbin" collimator.

The bobbin collimator 30 is supported by an annular support plate 33 by securing one of the flanges 31 to an axial end face of the plate 33. The support plate 33 with the bobbin collimator 30 for use with position annihilation radiation and the support plate 10 with the swing collimator ring 5 for use with gamma radiation are connected by means of studs 34 in an axially aligned and spaced apart relation so that the bobbin collimator 30 and the swing collimator ring 5 are axially aligned and arranged close to each other.

An annular support plate 18 is provided at one axial end surface thereof with a plurality of radial ribs 19 axially projecting from the surface of the support plate 18. The ribs 19 are circumferentially spaced apart to define between each adjacent two ribs a space 19' in which one of the detectors $3_1, 3_2, \ldots 3_i, \ldots 3_n$ is fitted, so that the detectors are radially directed and circumferentially arranged side by side to form the detector ring 3, with their planes 3a on which the radiation is incident facing radially inwardly to define a circular aperture 20 concentric with the central aperture 18' of the annular support plate 18.

The plate 18 is connected by studs 21 to an annular support plate 22 which is in turn mounted by means of a bearing 22' on a flange 23 formed in a gantry 24 which encloses all the abovementioned and other component parts of the apparatus. A base 25 supports the gantry 24.

The studs 34 connecting the two support plates 10 and 33 are supported in through bores 35 formed in the plate 18 axially slidably so that by displacing the combined support plates 10 and 33 axially it is possible to selectively position the swing collimator ring 5 for use with gamma radiation emitting radionuclides and the bobbin collimator 30 for use with positron emitting radionuclides radially inwardly of and close to the detector ring 3.

For such axial displacement of the combined plates 10 and 33, a screw stud 36 supported by the support plate 22 through a radial bearing 37 is threaded through the support plate 33 as at 38 and provided at one end thereof with a gear 39 meshing with a drive pinion 40 which is driven by a suitable drive 41 including a reversible motor $M_3$ and mounted on the support plate 22 by a bracket 42.

As can be easily understood, when the motor $M_3$ is rotated in one direction, the threaded stud 36 is rotated to displace the combined plates 10 and 33 axially in one direction, say, leftward in FIG. 1 thereby to bring the swing collimator ring 5 into radial alignment with or concentric relation to the detector ring 3 inwardly thereof. When the motor $M_3$ is rotated in the opposite direction, the threaded stud 36 is rotated in the opposite direction to displace the combined plates 10 and 33 axially in the opposite direction, that is, rightward in FIG. 1 thereby to bring the collimator 30 into radial alignment with or concentric relation to the detector ring 3 inwardly thereof in place of the swing collimator ring 5.

A drive roller 26 frictionally contacts the peripheral surface of the annular support plate 22 and is rotated by a driving device 27 including a reversible motor $M_2$ thereby to change the circumferential position of the support plate 22 and all the component parts mounted thereon or connected thereto.

The gantry 24 has a central tunnel 28 in which the head holder T can be placed. The tunnel 28 is formed with a circumferential slot 28' in radial alignment with the detector ring 3 inwardly thereof. The head holder T is attached to a bed B which is slidably supported on a base 29.

A slice mask 43 made of a material permeable to radiation is supported by means of a suitable support member 44 secured to the support plate 10 radially between the detector ring 3 and the slot 28' in the wall of the tunnel 28, with a circumferential space between the mask 43 and the detector ring 3 sufficient to accommodate the swing collimator ring 5 or the bobbin collimator 30 therein.

In operation, with the swing collimators $5_1, 5_2, \ldots 5_i, \ldots 5_n$ positioned in radial alignment with and in front of the detectors $3_1, 3_2, \ldots 3_i, \ldots 3_n$, respectively, as the plates 5a and 5b of the swing collimators are swung by rotating the motor $M_1$, the gamma radiation emerging from the head 1 of a patient P being examined passes through the spaces between the plates 5a and 5b to enter the detectors. The data collected by the detectors are transferred to a computer 45 through an interface 46 so as to reconstruct a tomographic image of the head, which is displayed on a suitable display unit 47 and recorded by a storage device 48 such as a magnetic disk.

When it is desired to use the bobbin collimator 30, the motor $M_3$ is energized to axially displace the combined support plates 10 and 33 to remove the swing collimators from before the detectors and instead bring the bobbin collimator 30 into concentric relation to the detector ring 3. The positron annihilation radiation emerging from the patient's head passes between the annular flanges 31 and 31 of the bobbin collimator 30 to enter the detectors. The data collected by the detectors are processed by the computer 45 to reconstruct a tomographic image of the head 1 in the same manner as mentioned just above. The computer also controlls the motors $M_1$, $M_2$ and $M_3$.

Having illustrated one preferred embodiment of the invention, there may be changes and modifications thereof. For example, as the swing collimators disclosed in copending patent application may be used for gamma radiation and any other suitable types of collimators may be used for positron annihilation radiation. The mechanism for displacing the two kinds of collimators is not limited to the one employed in the illustrated embodiment.

As described above in detail, the apparatus of the invention is very convenient and economical since it can be used with different kinds of radionuclides to obtain tomographic images of the object to be examined.

What we claim is:

1. An emission computed tomograph comprising: means for supporting an object to be examined at a predetermined position, said object having taken therein a radionuclide that emits radiation; a plurality of radiation detectors so arranged as to surround said predetermined position; a plurality of collimator means each for use with a different kind of radionuclides and each so arranged as to surround said position; means for supporting said plurality of collimator means in axial alignment; means for causing said supporting means to be axially displaced relative to said detectors so that each of said collimator means can alternatively be brought into radial alignment with and operative relation to said detectors.

2. The apparatus of claim 1, wherein said collimator means comprises first collimator means for use with a first kind of radionuclides and second collimator means for use with a second kind of radionuclides.

3. The apparatus of claim 2, wherein said first kind of radionuclides emit gamma radiation and said second kind of radionuclides emit positrons.

4. The apparatus of claim 3, wherein said first collimator means comprises a plurality of collimators for collimating gamma radiation to be detected by said detectors; and said second collimator means comprises a single collimator so shaped as to collimate positron annihilation radiation to be detected by said detectors.

5. The apparatus of claim 4, wherein each of said collimators of said first collimator means comprises a pair of thin plates made of a material capable of blocking penetration of gamma radiation therethrough and extending radially inwardly so as to define the direction in which the gamma radiation from said object is incident on each of said detectors, said plate having an axis of rotation at a border between each adjacent two of said detectors so that said plates are swingable over a predetermined angle sufficient to cover the whole of said object.

6. The apparatus of claim 4, wherein said single collimator of said second collimator means comprises a pair of flanges made of a material capable of blocking penetration of positron annihilation radiation therethrough, said flanges being axially spaced apart and fixed to the opposite axial end of a hollow cylindrical body made of a material permeable to positron annihilation radiation and surrounding said object to be examined.

* * * * *